United States Patent [19]

Chauvette et al.

[11] Patent Number: 5,562,649
[45] Date of Patent: Oct. 8, 1996

[54] ABSORBENT PERF-EMBOSSED DEBONDED PULP BOARD

[75] Inventors: Gaetan Chauvette, Longueuil; Sylvie Boisse, Ville d'Anjou; Yvon Levesque, Montreal, all of Canada

[73] Assignee: Johnson & Johnson Inc., Montreal, Canada

[21] Appl. No.: 149,142

[22] Filed: Nov. 3, 1993

Related U.S. Application Data

[63] Continuation of Ser. No. 3,931, Jan. 4, 1993, abandoned, which is a continuation of Ser. No. 529,058, May 25, 1990, abandoned.

[51] Int. Cl.$^6$ ............................ A61F 13/15; D21F 11/00
[52] U.S. Cl. ......................... 604/375; 604/358; 604/374; 604/383; 162/158
[58] Field of Search ......................... 604/368, 372, 604/374, 375, 378; 162/158

[56] References Cited

U.S. PATENT DOCUMENTS

| | | | |
|---|---|---|---|
| 3,554,862 | 1/1971 | Hervey et al. | 162/158 |
| 3,556,931 | 1/1971 | Champaigne | 604/368 |
| 3,563,243 | 2/1971 | Lindquist | 128/287 |
| 3,812,000 | 5/1974 | Salvucci et al. | 162/111 |
| 4,035,217 | 7/1977 | Kennette et al. | 604/372 |
| 4,053,217 | 7/1977 | Kennette et al. | 156/279 |
| 4,144,122 | 3/1979 | Emanuelsson et al. | 162/158 |
| 4,259,958 | 4/1981 | Goodbar | 604/374 |
| 4,432,833 | 2/1984 | Breese | 162/100 |
| 4,551,142 | 11/1985 | Kopolow | 604/368 |
| 4,581,058 | 4/1986 | Fenyes et al. | 71/67 |
| 4,596,567 | 6/1986 | Iskra | 604/368 |
| 4,605,402 | 8/1986 | Iskra | 604/368 |
| 4,900,377 | 2/1990 | Redford et al. | 162/146 |

FOREIGN PATENT DOCUMENTS

| | | |
|---|---|---|
| 925337 | 5/1973 | Canada. |
| 151018 | 8/1985 | European Pat. Off. ........ A61F 13/18 |

*Primary Examiner*—John G. Weiss
*Assistant Examiner*—Dennis Ruhl
*Attorney, Agent, or Firm*—James P. Barr

[57] ABSTRACT

A highly absorbent and flexible cellulosic pulp board comprising a perf-embossed cellulosic pulp board which has incorporated therein a hydrophilizing and softening effective amount of a debonding agent wherein the density of the board is in the range of about 0.1 to 1.0 g/cc and its method of making and method of use in disposable absorbent products.

27 Claims, No Drawings

ABSORBENT PERF-EMBOSSED DEBONDED PULP BOARD

This is a continuation of application Ser. No. 08/003,931 filed Jan. 4, 1993, now abandoned, which is a continuation of application Ser. No. 07/529,058, filed May 25, 1990, now abandoned.

FIELD OF THE INVENTION

This invention is directed to highly absorbent and flexible pulp board products. More particularly, the flexible and absorbent board is a perf-embossed and debonded cellulosic pulp board which provides strong, thin, moisture absorbent cores for disposable absorbent products such as sanitary napkins, wound dressings, bandages, incontinent pads, disposable diapers and the like. The invention also provides methods of preparing such highly absorbent and flexible cellulosic pulp boards and their method of use in disposable absorbent products.

BACKGROUND OF THE INVENTION

Many disposable absorbent articles use fluff pulp as the absorbent core. Such cores are generally soft, flexible and absorbent but tend to be bulky and thick and have poor wicking properties.

An absorbent structure that has poor wicking properties may increase the likelihood of failure of the absorbent product to hold and contain body fluids. Body fluids will be localized to a certain area of a poorly wicking absorbent core and cause saturation in such area whereby excess fluid may overflow through an external surface of the absorbent product. This overflow may contact the user's garment and cause stains or contact the user's body and cause wet discomfort or rash.

It is therefore desirable to provide an absorbent core for disposable absorbent articles which can wick away body fluids from the point of contact with the absorbent core and spread it throughout the absorbent core to more efficiently utilize the entire surface area of the absorbent core. The improved wicking properties of such an absorbent core provides the capacity for fluids to travel by capillary action throughout the surface area of the absorbent core and thus permit the use of thinner cores, since more absorbent surface area can be made available for absorbing body fluids by such wicking action. Thinner structures of absorbent cores may prove to be more comfortable for the user and less unsightly or obvious when worn under clothes.

Absorbent cores with excellent wicking properties comprising peat moss and wood pulp composite materials are described, for example, in U.S. Pat. Nos. 4,170,515; 4,226,237; 4,215,692; 4,507,122; 4,676,871; and 4,473,440. In accordance with the teachings of these patents, an absorbent structure comprising peat moss as a primary absorbent component is formed as a board by air or wet laying of fibers and calendaring the board to obtain a relatively thin, i.e. from about 0.01 to 0.10 inch thick, relatively dense, i.e. from about 0.2 to 1.0 gram/cm$^3$ sheet-like structure. Such absorbent peat moss boards may be processed to increase the flexibility thereof by subjecting such boards to perf-embossing as described in U.S. Pat. No. 4,596,567 or microcorrugating as described in U.S. Pat. No. 4,605,402.

The peat moss boards thus formed have a large proportion of extremely tiny pores and capillaries which give them the ability to absorb and retain an enormous capacity of fluid. The peat moss pores swell as they absorb fluid, however, this swelling does not cause a loss of capacity for absorbing fluid. Rather, the swelling contributes to the ability of the board to retain fluid while generally maintaining the structural integrity of the absorbent structure in use.

The wicking properties of the above-described peat moss boards provide the ability for the boards to be highly absorbent and thin. The flexibility of peat moss board may be improved by perf-embossing and/or microcorrugating as described above.

While peat moss boards make excellent absorbent and wicking cores for disposable absorbent articles, there are limitations to their production and use. Peat moss board may not be readily available particularly in areas which lack the critical raw material, i.e. peat moss or sphagnum moss of desirable age, structure and moisture content. Peat moss board also is relatively dark in color and may not be aesthetically acceptable for use in all absorbent products. It is, therefore, desirable to provide a thin, absorbent and wicking core for disposable absorbent articles which may be substituted for peat moss boards.

Attempts to utilize other cellulosic pulp boards such as kraft wood pulp boards as absorbent cores have not been successful because they tend not to have as much absorbent capacity as peat moss composite boards but more importantly cannot be sufficiently softened for their intended use. While such kraft wood pulp board's flexibility and other characteristics may be improved by perf-embossing or microcorrugating techniques, such products still do not provide a desirable combination of absorption capacity and fluid penetration, wicking rates and most importantly a sufficient degree of flexibility to be useful in disposable absorbent products, particularly, sanitary napkins.

It is, therefore, an object of the present invention to provide a cellulosic pulp board which does not utilize peat moss in its structure but has sufficient absorption capacity, wicking characteristics as well as advantageously short fluid penetration time and possessing optimal flexibility for use in disposable absorbent articles, particularly sanitary napkins. Optimal flexibility of such products requires that the product be comfortably soft and flexible to the wearer but stiff and strong enough to substantially retain its original shape in use or after wetting.

SUMMARY OF THE INVENTION

The foregoing object of providing a thin, strong, highly absorbent, and flexible absorbent core with good wicking properties has now been accomplished in accordance with the compositions, products and methods of the present invention.

In accordance with the purposes of the invention, as embodied and fully described herein, the invention comprises a highly absorbent and flexible perf-embossed cellulosic pulp board which has incorporated therein a hydrophilizing and softening effective amount of a debonding agent wherein the density of the board is in the range of about 0.1 to 1.0, preferably 0.2 to 0.3 g/cc. The perf-embossed and debonded absorbent pulp board of the invention has good wicking characteristics and when incorporated into a disposable absorbent product, e.g. a sanitary napkin, is sufficiently flexible to be worn comfortably. In preferred embodiments of the invention, the dry thickness of the board is in the range of about 0.030 to 0.10, and preferably, about 0.045 to 0.070 inches and more preferably about 0.05 inches; the dry tensile strength of the board is at least about 2.5 lbs/inch in the cross-direction and 4.0 lbs/inch in the machine direction. In other preferred embodiments of the invention, the cellulosic pulp is a sulfate, sulfite, bleach, unbleached or kraft wood pulp. The preferred debonding agent incorporated into the pulp board is a cationic or anionic surface active agent or mixture thereof and more particularly a quaternary ammonium salt in an amount in the range of about 0.1 to 1.5 percent, preferably about 0.3 to about 0.5 percent by weight of the total dry weight of the pulp board. For purposes of the present invention dry board or dry pulp fibers have a moisture content of less than about 12% and preferably about 6 to 7%.

As embodied and broadly described herein, the invention further comprises disposable absorbent products having an absorbent core with good wicking characteristics comprising the flexible and absorbent perf-embossed cellulosic pulp board which has incorporated therein a hydrophilizing and softening effective amount of a debonding agent wherein the density of the board is in the range of about 0.1 to 1.0 g/cc and the flexibility of the board is sufficient to be worn comfortably by a wearer of the disposable absorbent product. In preferred embodiments of the invention, the disposable absorbent product is selected from the group consisting of sanitary napkins, incontinent products, diapers, and wound dressings. In more preferred embodiments of the invention, a thin, absorbent and flexible sanitary napkin is provided which has an improved absorbent layer comprising a perf-embossed cellulosic pulp board which has incorporated therein a hydrophilizing and softening effective amount of a debonding agent. In most preferred embodiments of the invention the absorbent core is of optimal flexibility to be comfortable to the product wearer but stiff enough to substantially retain its original shape in use or after wetting.

As embodied and broadly described herein, the invention further comprises a method of preparing a highly absorbent and flexible cellulosic pulp board comprising the steps of:

(a) forming a cellulosic pulp board;

(b) incorporating a hydrophilizing and softening effective amount of a debonding agent in the cellulosic pulp board; and (c) perf-embossing the debonding agent containing pulp board of step (b) to reduce the stiffness of said pulp board.

In preferred embodiments of the method of the invention, the fluid penetration time of the board is shortened and the absorbent capacity of the board is increased. In preferred embodiments of the invention, the debonding agent is a quaternary ammonium composition and the cellulosic pulp utilized is a sulfate, sulfite, bleached, unbleached or kraft wood pulp. In further embodiments of the invention, the pulp board is subjected to an additional mechanical step comprising, for example, microcorrugating or other mechanical processing of the pulp board including subsequent perf-embossing steps.

As embodied and broadly described herein, the invention further comprises a method of providing good fluid absorption in a thin and comfortable sanitary napkin comprising a step of incorporating as an absorbent core in the sanitary napkin a cellulosic pulp board of a dry thickness of about 0.030 to 0.10 inches, a density of about 0.2 to 1.0 g/cc, and good wicking characteristics comprising a perf-embossed cellulosic pulp board which has incorporated therein a hydrophilizing and softening effective amount of a debonding agent.

DETAILED DESCRIPTION OF THE INVENTION

Reference will now be made in detail to preferred embodiments of the invention, examples of which are illustrated in the following examples section.

To achieve the object of the invention of providing a highly absorbent, flexible and good wicking core for disposable absorbent products which may be an economical and suitable replacement for peat composite boards, the present inventors have made the unexpected discovery that cellulosic pulp board, particularly wood pulp board, which has incorporated therein a debonding agent and is subjected to a perf-embossing treatment, will provide a highly absorbent and flexible absorbent core whereby the density is in a range of 0.1 to 1.0 g/cc, it has an advantageously short fluid penetration time and is of optimal flexibility.

The preferred cellulosic pulp utilized in accordance with the invention is a sulfate, sulfite or kraft wood pulp but other cellulosic pulps may be used, such as, for example, unbleached wood pulp or wood pulp bleached by chlorine processes or hydrogen peroxide, and chemical thermal mechanical pulp.

It is important that the wood pulp board have incorporated therein a sufficient amount of a chemical debonding agent effective to provide hydrophilic and softening characteristics to the pulp board such that the absorbency and comfort potential of the pulp board is increased for use as an absorbent core in disposable absorbent products. Examples of absorbent products include, but are not limited to sanitary napkins, diapers, incontinence products, wound dressings, and bandages. The highly absorbent and flexible cellulosic pulp boards of the invention may also be utilized as packing materials to provide dry shipment of goods which may exude moisture in shipment or storage. Such goods might include food items such as meat or fish.

Chemical debonding agents are known in the paper making art as well as in the pulp fluff art. Such debonding agents are mixed with cellulosic fibers to inhibit the formation of bonds between the fibers after forming. Debonding agents are described and disclosed in U.S. Pat. No. 4,482,429 at col. 4, lines 8–36; U.S. Pat. No. 4,144,122; and U.S. Pat. No. 4,432,833. The entire disclosures of these references are hereby incorporated herein by reference.

The reduction of interfiber bonding in products formed from wood pulp such as paper or pulp boards, increases the ease with which these products may be mechanically worked, for example, creping of paper. Debonding agents have been previously used in pulp board to reduce the amount of mechanical energy required to macerate the pulp board into pulp fluff for use in fluff absorbent cores.

Debonding agents can be incorporated into pulp board either by incorporation into the pulp slurry prior to formation of the pulp board or during the forming process of the pulp board. For example, U.S. Pat. No. 3,556,931 discloses a process by which a wet cellulosic pulp batt is treated with a dilute aqueous solution of cellulosic fiber debonding agent to penetrate a surface zone of the batt to decrease the coherence of fibers for each other. The pick-up of the debonding agent is about 1% of the dry weight of pulp fibers. The batt is flexed by simply bending it about an axis transverse to the length of the bart to further open up its surface zone. The bart is then impinged with a gas stream which is nonreactive to the fibers to further disrupt bonds in the surface zone of the batt to provide a layered absorbent and soft cellulosic fibrous body whereby an outer surface of the batt is rendered soft and fluffy with a density of about 0.06 g/cc and a more compacted interior zone is provided with a density of about 0.18 g/cc. U.S. Pat. No. 3,554,862 discloses that chemical debonding agents may be added to pulp furnish, slurry or sheet prior to fiberizing by mechanical action to more easily form a fluffier and loftier material versus fiberization of wood pulp that has not been treated with a debonding agent. The disclosures of these two patents relating to cationic debonding agents and their methods of use for incorporation into pulp products is hereby incorporated herein by reference.

In addition to the debonding agents disclosed in U.S. Pat. Nos. 3,556,931 and 3,554,862 identified above, any hydrophilizing and softening pulp debonding agent may be utilized. Preferably, the debonding agent is a cationic or anionic surface active agent and more preferably a quaternary ammonium compound. Any agent which inhibits the interfiber bonding of cellulosic pulp fibers to effectively soften and hydrophilize a pulp sheet may be useful in accordance with the present invention. U.S. Pat. No. 4,432,833 discloses various hydrophilic quaternary amine debonders and U.S. Pat. Nos. 3,972,855 and 4,144,122 disclose various debonding agents including the commercially available BEROCELL 584 debonding agent which is a particularly preferred debonding agent for use in the present invention. The disclosure of the various debonding agents in these patents is hereby incorporated herein by reference.

The present invention provides a unique method of treating wood pulp boards or sheets which have a hydrophilizing and softening effective amount of a debonding agent incorporated therein. Such pulp sheets are commercially available from, for example, Weyerhaeuser as NBFA Kraft which incorporates about 0.3 to 0.45% of BEROCELL 584 brand debonding agent by weight on dry pulp and ITT as RAY-FLOC-XJ and-J MX Pulp which incorporates on dry pulp about 0.32% and 0.13% of BEROCELL 584 brand debonding agent, respectively. These commercial sheets are normally subjected to fiberizing or macerating to produce fluffy pulp fibers. Such debonded pulp boards have a density of about 0.48 to 0.49 g/cc and are not considered as likely candidates as absorption cores because of their high stiffness. The present inventors have found, contrary to such conventional knowledge of those skilled in the absorption art, that non-fiberized debonded pulp sheets of density above 0.3 g/cc may be mechanically treated to provide useful absorbent cores for disposable absorbent articles.

The amount of debonding agent incorporated into the pulp boards useful in the practice of the present invention is an amount effective to provide sufficient hydrophilic and softness properties in the board for advantageous treatment of the board to provide useful absorbent cores in accordance with the invention. In preferred embodiments of the invention the debonding agent is present in amounts of from 0.1 to 1.5% and more preferably 0.3 to 0.5%. These amounts may change, however, depending on the type of pulp and/or debonding agent(s) used.

It has been surprisingly found by the present inventors that the mechanical treatment of debonded pulp board with a perf-embossing process which is described, for example, in U.S. Pat. No. 4,596,567 can reduce the stiffness of such debonded pulp board to acceptable levels for use as an absorbent core in disposable absorbent products. The entire disclosure of this patent is hereby incorporated herein by reference. This combination of debonding and perf-embossing provides a synergistic effect to increase absorption and flexibility properties of the pulp board and provide an unexpected shortening of fluid penetration time and an increase in the wickability characteristics of the board to provide a highly absorbent and flexible absorbent core suitable for disposable absorbent articles including sanitary napkins.

The debonded and perf-embossed wood pulp board of the invention can be provided in ultra-thin dimensions as thin as 0.010 inches but preferably in the range of 0.030 to 0.10 inches. These thicknesses are for unused or dry (moisture content less than about 12%, preferably about 6 to 7%) product. This thickness will increase in use as fluids are absorbed but such increases will not generally effect absorption capacity or comfort.

The pulp board of the invention provides high absorption capacity and shorter fluid penetration time due to the hydrophilic debonded nature of the board and an increase in surface area provided by the perf-embossing. The increase in flexibility is of the utmost importance to provide an absorbent core in a sanitary napkin which is comfortable to the wearer and can conform to various body shapes and movements in use. The optimal flexibility achieved in accordance with the invention provides a board that is flexible enough to meet comfort criteria but stiff enough to resist product bunching and deforming in use and/or upon wetting. Such optimal flexibility and strength contributes to provide better fit for improved protection against overflow leakages and retention of product shape through use or wetting.

A further surprising advantage of the debonded and perf-embossed cellulosic pulp absorbent core over pulp fluff and even peat composite absorbent cores is the integrity and high tensile strength of the pulp core and its resistance to deterioration through wetting and use. Absorbent cores produced in accordance with the present invention preferably have a dry tensile strength of at least about 2.5 lbs/inch in the cross-direction and about 4.0 lbs/inch in the machine direction, preferably about 2.9 lbs/inch in the cross-direction and 4.8 lbs/inch in the machine direction.

The outstanding combination of absorption, flexibility and wicking characteristics of the absorbent core of the invention provides sanitary napkins capable of absorbing menstrual or other body fluids quickly and efficiently and retaining fluid in the absorbent structure of the napkin so as to limit failure. Sanitary napkins utilizing absorbent cores of the invention are flexible and conformable, yet resistant to bunching, twisting, and deterioration through active use. The absorbent core of the invention can be utilized as an insert or as an entire surface bilayer of a sanitary napkin. For example, the absorbent core of the invention can be utilized as a reservoir layer or insert in conjunction with a cover and transfer layer or because of its short fluid penetration time it may be used adjacent only a cover layer whereby the absorbent core of the invention serves the dual function of a transfer and reservoir layer. Examples of a sanitary napkin construction that may utilize absorbent cores in accordance with the invention are disclosed in U.S. patent application Ser. Nos. 389,710 and U.S. Pat. No. 4,226,237. The entire disclosures of these references are hereby incorporated herein by reference.

The pulp board of the invention in addition to being perf-embossed and treated with a debonding agent, may also be subjected to other mechanical processing such as micro-corrugating as described in U.S. Pat. No. 4,605,402 the entire disclosure of this patent is hereby incorporated herein by reference. Further, the debonded and perf-embossed wood pulp board of the invention may also be treated with softening agents, such as glycerine or lanolin in amounts of about 1.0% add-on of total dry fiber weight basis.

In addition to softening agents other absorbent materials such as fibers or "superabsorbent" polymers may be incorporated into the matrix spaces of the absorbent core structure. Such fibers and polymers are described, for example, in U.S. Pat. No. 4,559,050 the entire disclosure of which is hereby incorporated herein by reference. Further, superabsorbent laminates may be provided in combination with the debonded pulp board to provide extra absorption capacity such as, for example, in incontinence products.

EXAMPLES

The invention will now be illustrated by examples. The examples are not intended to be limiting of the scope of the present invention but read in conjunction with a detailed and general description above provides further understanding of the present invention and an outline of a process for preparing the absorbent and flexible cellulosic pulp boards of the invention and a sanitary napkin which comprises such pulp board as its absorbent core.

Examples 1–3

Preparation of Absorbent and Flexible Cellulosic Pulp Board

Debonded cellulosic pulp boards are obtained commercially from, for example, Weyerhaeuser which is designated as NBFA Kraft pulp or ITT which is designated as RAYFLOC-XJ or RAYFLOC-J MX. Technical characteristics of these pulp boards are provided below in Table 1.

TABLE 1

| | Debonded Pulp Boards | | |
|---|---|---|---|
| | Ex. 1 NBFA | Ex. 2 RAYFLOC-XJ | Ex. 3 RAYFLOC-J MX |
| Density | .49 g/cc | .48 g/cc | .48 g/cc |
| Thickness | 1.51 mm | 1.35 mm | 1.31 mm |
| Basis Weight | 680 g/m² | 635 g/m² | 635 g/m² |
| Weight % of Debonding Agent (BEROCELL 584) by weight in dry pulp | 0.3–0.4 | 0.32 | 0.13 |

The boards of Examples 1–3 are treated by perf-embossing as described in U.S. Pat. No. 4,596,567 which has previously been incorporated herein by reference.

The perf-embossing or tenderizing process is a mechanical operation which first perforates the pulp board, then embosses the resulting material in the X (machine direction) and Y (cross-direction) directions. The "perf" operation (first step) is done to open the structure of cellulosic material. The interference between parallel rolls is set from 10 to 120 mm, and more preferably from 70 to 95 mm. A second step consists in embossing the perforated material in the machine direction (MD). This step significantly reduces the thickness of the material and creates longitudinal "channels" on the board. The interference between parallel rolls is to be set from 10 to 70 mm, and more preferably from 30 to 40 mm.

A third step consists of embossing the resulting material in the cross direction (CD). This means a perpendicular impact to the second step operation. This creates lateral channels making the material flexible in the X and Y directions. The interference between parallel rolls is to be set from 10 to 70 mm, and more preferably from 25 to 35 mm.

The perf-embossed boards prepared in accordance with the procedures set out above for Examples 1–3 have the characteristics as described in Table 2 below.

TABLE 2

| | Perf-Embossed (PE) Debonded Pulp Boards | | |
|---|---|---|---|
| | PE Ex. 1 | PE Ex. 2 | PE Ex. 3 |
| Density | 0.20 g/cc | 0.315 g/cc | 0.28 g/cc |
| Thickness | 3.05 mm | 2.03 mm | 2.14 mm |
| Absorption Time 15 cc | 27.1 sec | N.A. | 25.8 sec |

The tensile strength of Example 1 is about 2.9 lbs/inch in the cross-direction and about 4.8 lbs/inch in the machine direction.

In addition to the above, the perf-embossing process increases the dimension of the pulp boards in the cross direction by about 5 to 7%.

Example 4

Preparation of a Sanitary Napkin comprising an Absorbent and Flexible Cellulosic Pulp Board as it Absorbent Core A perf-embossed absorbent core prepared in accordance with Example 1 having dimensions of thickness 0.082", length 7⅝" and width 1¹⁵⁄₁₆" is incorporated into a layered sanitary napkin product as an insert or total surface in accordance with the materials and procedures described in U.S. Pat. No. 4,226,237, which has previously been incorporated by reference herein, to produce a thin sanitary napkin of acceptable absorption, flexibility and comfort for its intended use.

Sanitary napkins produced in accordance with Example 4 were found in use to possess similar absorption and wicking capabilities as that of a peat moss composite board absorbent core. The sanitary napkin of the invention is found to be objectively somewhat less flexible than peat moss composite absorbent core napkins, but this was not observed as significantly affecting comfort for wearers in use. It was further found that sanitary napkins in accordance with the invention are surprisingly more resistant to bunching and deforming than peat moss composite or pulp fluff absorbent core napkins leading to better overall performance in terms of protection from leakage and retention of product shape.

The scope of the present invention is not limited by the description, examples and suggested uses herein and modifications can be made without departing from the spirit of the invention. For example, additional embossing patterns that provide either aesthetic or functional qualities to the debonded and perf-embossed cellulosic pulp boards of the invention may be provided. The absorbent cores of the present invention may also be utilized in diverse products including incontinence pads, absorbent cores as inserts for diapers or tampons or as dessicants for packing material which must be kept dry during shipping or storage.

Application of the products and methods of the present invention for sanitary and other healthcare uses can be accomplished by any sanitary protection, incontinence, medical, and absorbent methods and techniques as are presently or prospectively known to those skilled in the art. Thus, it is intended that the present invention cover the modifications and variations of this invention provided that they come within the scope of the appended claims and their equivalents.

What is claimed is:

1. A highly absorbent and flexible cellulosic pulp board comprising a non-fiberized cellulosic pulp board which has incorporated therein a hydrophilizing and softening effective amound of a debonding agent, which after forming is pref-embossed to decrease its stiffness, wherein the density of the board is in the range of about 0.1 to 1.0 grams/cubic centimeter.

2. The pulp board of claim 1 wherein the pulp board has a dry tensile strength in the range of at least about 2.5 lbs/inch in a cross-direction and about 4.0 lbs/inch in a machine direction.

3. The pulp board of claim 1 wherein the pulp board has a dry thickness in the range of about 0.030 to 0.10 inches.

4. The pulp board of claim 1 wherein the pulp board has a density in the range of about 0.2 to 0.3 grams/cubic centimeter and a thickness in the range of 0.045 to 0.070 inches.

5. The pulp board of claim 1 wherein the debonding agent is a cationic or anionic surface active agent or combination thereof.

6. The pulp board of claim 1 wherein the debonding agent is a quaternary ammonium salt and is present in an amount in the range of about 0.1 to 1.5 percent by weight of the total dry weight of the cellulosic pulp board.

7. The pulp board of claim 5 wherein the debonding agent is present in an amount of from 0.3 to 0.5 percent by weight of the total dry weight of the cellulosic pulp board.

8. The pulp board of claim 1 wherein the cellulosic pulp board contains cellulosic pulp selected from the group consisting of sulfate, sulfite, kraft, bleached and unbleached wood pulp and chemical thermal mechanical pulp.

9. The pulp board of claim 1 wherein additional softening agents or absorbent materials are incorporated therein.

10. A disposable absorbent product having an absorbent core comprising the cellulosic pulp board of claim 1 wherein the disposable absorbent product is selected from the group consisting of sanitary napkins, incontinence products, diapers, and wound dressings.

11. Packing materials comprising an absorbent core in accordance with claim 1.

12. A thin, absorbent and flexible sanitary napkin having an improved absorbent layer comprising a non-fiberized perf-embossed cellulosic pulp board which has incorporated therein a hydrophilizing and softening effective amount of a debonding agent whereby the pulp board is sufficiently flexible to be worn comfortably by a wearer of said sanitary napkin.

13. The sanitary napkins of claim 12 wherein the non-fiberized, perf-embossed cellulosic pulp board has a thickness in the range of about 0.03 to 0.10 inches and density in the range of about 0.1 to 1.0 grams/cubic centimeter.

14. The sanitary napkin of claim 12 wherein the non-fiberized, perf-embossed cellulosic pulp board has a thickness of about 0.045 to 0.070 inches and density of 0.2 to 0.3 g/cc.

15. The sanitary napkin of claim 12 wherein the perf-embossed cellulosic pulp board is wood pulp.

16. The sanitary napkin of claim 12 wherein the debonding agent is a quarternary ammonium salt and the amount incorporated into the cellulosic pulp board is about 0.1 to 1.5 percent by weight of the total dry weight of the non-fiberized, perf-embossed cellulosic pulp board.

17. A method of preparing a highly absorbent and flexible non-fiberized cellulosic pulp board comprising the step of:
(a) forming a non-fiberized cellulosic pulp board;
(b) incorporating a hydrophilizing and softening effective amount of a debonding agent in the cellulosic pulp board; and
(c) perf-embossing the debonding agent containing pulp board of step (b) to reduce the stiffness of said pulp board.

18. The method of claim 17 wherein the debonding agent is a cationic or anionic surface active agent or mixture thereof.

19. The method of claim 17 wherein additional softening agents or absorbing materials are incorporated into the cellulosic pulp board.

20. The method of claim 17 wherein the cellulosic pulp board is subject to an additional step comprising microcorrugating or other mechanical processing of said cellulosic pulp board.

21. A method of providing good fluid absorption in a thin and comfortable sanitary napkin comprising the step of incorporating as an absorbent and wicking core in the sanitary napkin a non-fiberized cellulosic pulp board of a dry thickness between about 0.045 to 0.070 inches and a density between about 0.1 to 1.0 grams/cubic centimeter, wherein said cellulosic pulp board incorporated therein a hydrophilizing and softening effective amount of a debonding agent and wherein said non-fiberized cellulosic pulp board containing said debonding agent is perf-embossed to reduce its stiffness.

22. The method of claim 21 wherein the cellulosic pulp board is a wood pulp board and its density is in the range of about 0.2 to 1.0 grams/cubic centimeter.

23. The method of claim 2 wherein the pulp board has a tensile strength of at least about 2.5 lbs/inch in a cross-direction and 4.0 lbs/inch in a machine direction.

24. The method of claim 21 wherein the debonding agent is a quaternary ammonium salt and is present in an amount of about 0.1 to 1.5 percent by weight of the total dry weight of the non-fiberized cellulosic pulp board.

25. The method of claim 21 wherein additional softening agents or absorbing materials are incorporated into the fiberized cellulosic pulp board.

26. The method of claim 21 wherein the non-fiberized, cellulosic pulp board is subjected to microcorrugating.

27. The method of claim 21 wherein the non-fiberized cellulosic pulp board is selected from the group consisting of sulfate, sulfite, bleached, unbleached and kraft wood pulp board and chemical thermal mechanical pulp.

\* \* \* \* \*

UNITED STATES PATENT AND TRADEMARK OFFICE
CERTIFICATE OF CORRECTION

PATENT NO. : 5,562,649

DATED : October 8, 1996

INVENTOR(S) : Gaetan Chauvette, Sylvie Boisse, Yvon Levesque

It is certified that error appears in the above-identified patent and that said Letters Patent is hereby corrected as shown below:

Column 10 - Line 38 - "2" should be "21"

Signed and Sealed this

Sixteenth Day of September, 1997

Attest:

BRUCE LEHMAN

Attesting Officer

Commissioner of Patents and Trademarks